United States Patent

[11] B 3,994,937
[45] Nov. 30, 1976

Wiechert et al.

[54] 15α,16α-METHYLENE-4-ESTREN-17β-OLS

[75] Inventors: Rudolf Wiechert; Hermann Steinbeck; Walter Elger, all of Berlin, Germany

[73] Assignee: Schering Aktiengesellschaft, Berlin & Bergkamen, Germany

[22] Filed: June 28, 1974

[21] Appl. No.: 484,068

[44] Published under the second Trial Voluntary Protest Program on March 2, 1976 as document No. B 484,068.

Related U.S. Application Data

[63] Continuation of Ser. No. 331,059, Feb. 9, 1973, abandoned.

[30] Foreign Application Priority Data

Feb. 11, 1972 Germany............................ 2207421

[52] U.S. Cl............................. 260/397.4; 260/239.5; 260/239.55 D; 260/239.55 R; 260/397.5; 424/238; 424/243
[51] Int. Cl.².......................... C07J 1/00; C07J 3/00
[58] Field of Search...................... 260/397.4, 397.5

[56] References Cited
UNITED STATES PATENTS

| | | | |
|---|---|---|---|
| 3,275,666 | 9/1966 | Siegmann...................... | 260/397.4 X |
| 3,469,008 | 9/1969 | Schmidt et al...................... | 424/243 |
| 3,470,160 | 9/1969 | Schmidt et al.................. | 260/239.55 |
| 3,525,757 | 8/1970 | Schmidt et al.................. | 260/397.4 |
| 3,749,742 | 7/1973 | Wiechert et al................. | 260/397.4 |

*Primary Examiner*—Ethel G. Love
*Attorney, Agent, or Firm*—Millen, Raptes & White

[57] ABSTRACT

15α,16α-methylene-4-estren-17β-ols of the Formula

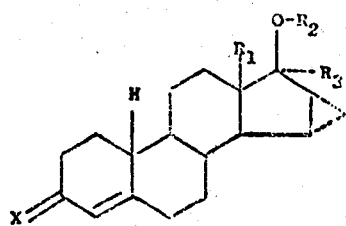

wherein $R_1$ is lower alkyl, $R_2$ is hydrogen or an acyl residue, $R_3$ is hydrogen or a substituted or unsubstituted, saturated or unsaturated monovalent lower aliphatic hydrocarbon, and X is oxygen or the group $H,OR_4$, wherein $R_4$ is hydrogen or an acyl residue, have useful anabolic, androgenic, and/or gestagenic activity.

25 Claims, No Drawings

15α,16α-METHYLENE-4-ESTREN-17β-OLS

This is a continuation of application Ser. No. 331,059, filed Feb. 9, 1973, now abandoned.

BACKGROUND OF THE INVENTION

This invention relates to new steroids. More particularly, this invention relates to 15α,16α-methylene-4-estren-17β-ols having useful pharmaceutical properties.

Anabolic and androgenically active steroids are well known in experimental biology and clinical medicine; for example, testosterone and its derivatives are widely used in veterinary medicine to treat androgenic hormone deficiencies, impotence, testicular deficiency and the like, and in clinical medicine to treat androgen deficiency or in cases where an anabolic effect is desired, e.g., senile osteoporosis, burns, etc. Testosterone propionate, described inter alia in U.S. Pat. Nos. 2,311,067, 2,374,369 and 2,374,370 is widely accepted as the standard of comparison for anabolic and androgenic activity but, while generally suitable for veterinary and clinical applications, exhibits the deficiency of having to administer a relatively high dosage of active substance.

Gestagenically effective steroids such as 18-methyl-17α-ethinyl-19-nortestosterone are widely used contraceptive agents, but due to their recognized adverse androgenic side effects, there is an interest in developing new gestagenic steroids having higher activity and/or reduced side effects.

OBJECTS OF THE INVENTION

Accordingly, it is an object of this invention to provide new steroid compounds having anabolic and androgenic activity.

Another object of this invention is to provide new steroid compounds having gestagenic activity.

A further object of this invention is to provide pharmaceutical compositions containing anabolicly and androgenically effective amounts of the compounds of this invention.

An additional object of this invention is to provide pharmaceutical compositions containing gestagenically effective amounts of the compounds of this invention.

Upon further study of the specification and appended claims, further objects and advantages of this invention will become apparent to those skilled in the art.

SUMMARY OF THE INVENTION

Briefly, the above and other objects are attained in one aspect of this invention by providing 15α,16α-methylene-4-estren-17β-ols of Formula I

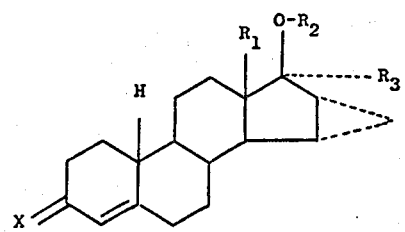

wherein $R_1$ is lower alkyl, $R_2$ is hydrogen or alkanoyl of 1-15 carbon atoms, $R_3$ is hydrogen or a substituted or unsubstituted, saturated or unsaturated monovalent lower aliphatic hydrocarbon, and X is oxygen or the group $H,OR_4$, wherein $R_4$ is hydrogen or alkanoyl of 1-15 carbon atoms.

DETAILED DISCUSSION

Compounds of this invention particularly preferred for anabolic and androgenic activity are compounds of Formula I wherein $R_3$ is hydrogen, while compounds of Formula I preferred for gestagenic activity are those wherein $R_3$ is a lower monovalent aliphatic hydrocarbon radical, i.e., alkyl, alkenyl or alkinyl of 1-5 carbon atoms, particularly preferred for gestagenic activity are those wherein $R_3$ is alkinyl.

$R_1$ in the above formula is alkyl of 1-5 carbon atoms, preferably methyl or ethyl.

$R_2$ and $R_4$ in the above formula are each independently hydrogen or alkanoyl of 1-15 carbon atoms, e.g., formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, etc.; branched carboxylic acids, e.g., trimethylacetic acid, diethylacetic acid, tert.-butylacetic acid, etc.

It will be appreciated by those skilled in the art that the many equivalents of these alkanoyl acyl radicals can be substituted therefor and are the equivalent thereof. Typically, such equivalent acyl radicals are those of any physiologically acceptable organic or inorganic acid derived by removal of a hydroxyl group therefrom, including carbocyclic or heterocyclic acyl containing one or two separate or fused rings, e.g., benzoyl, p-methoxybenzoyl, piperidino, morpholino and the like lower alkanoyls, cycloalkanoyl, etc.

Suitable equivalent acyl residues $R_2$ and $R_4$, respectively, are those derived from physiologically acceptable acids customarily employed for the esterification of steroid alcohols. These include but are not limited to organic alicyclic, aromatic or heterocyclic carboxylic acids having 1-18 carbon atoms which can be saturated or unsaturated, mono- or polybasic and/or substituted, e.g., by at least one of alkyl, hydroxy, oxo, amino or halogen. The customary inorganic acid residues can likewise be included herein, which include not are not limited to residues derived from sulfuric acid, phosphoric acid, etc. Specific such equivalent organic acids are cycloaliphatic carboxylic acids, e.g., cyclopentylacetic acid, cyclohexylacetic acid, etc.; substituted carboxylic acids, e.g., mono-, di-, and trichloroacetic acid, aminoacetic acid, diethylaminoacetic acid, piperidinoacetic acid, morpholinoacetic acid, lactic acid, etc.; polybasic carboxylic acids, e.g., succinic acid, adipic acid, etc.; aromatic carboxylic acids, e.g., benzoic acid, nicotinic acid, isonicotinic acid, furan-2-carboxylic acid, etc.

One group of preferred compounds of this invention is that in which at least one of $R_2$ and $R_4$ is hydrogen. Preferred alkanoic acids are those having 1-11 carbon atoms, particularly those having 1-8 carbon atoms, e.g., formic acid, acetic acid, propionic acid, butyric acid, valeric acid, caproic acid, enanthic acid and caprylic acid.

For the production of water-soluble preparations, the usually employed esters are suitable. Suitable esters include but are not limited to alkyl esters of succinic acid, adipic acid, sulfuric acid, and phosphoric acid, which are optionally converted into the alkali metal salts.

When $R_3$ of Formula I is other than hydrogen, preferred are monovalent aliphatic hydrocarbon radicals of 1–5 carbon atoms which can be saturated, i.e., lower alkyl; monoethylenically unsaturated, i.e., lower alkenyl; or monoacetylenically unsaturated, i.e., lower alkinyl. Suitable lower alkyl radicals include but are not limited to methyl, ethyl, n-propyl, n-butyl; of these, methyl and ethyl are preferred. Suitable lower alkenyl radicals include but are not limited to vinyl, propenyl, allyl, 1-butenyl, etc., which are ethylenically unsaturated, e.g., in the α-position. Suitable lower alkinyl radicals include but are not limited to ethinyl, 1-propynyl, 1-butadiynyl and the like, which are acetylenically unsaturated, e.g., in the α-position; of these, the ethinyl radical is preferred.

The monovalent aliphatic hydrocarbon radicals defined above can be unsubstituted or substituted in a suitable manner, e.g., by at least one of hydroxy or halogen, preferably chlorine; of these, the chloroethinyl radical is preferred.

Preferred compounds of this invention are those compounds of Formula I which meet one or more of the following criteria:

a. Compounds in which $R_1$ is methyl or ethyl;
b. Compounds in which $R_2$ is lower alkanoyl of up to 8 carbon atoms;
c. Compounds in which $R_3$ is hydrogen, ethinyl or substituted ethinyl;
d. Compounds in which $R_4$ is lower alkanoyl of up to 8 carbon atoms;
e. Compounds in which $R_2 = R_4$;
f. Compounds in which $R_3$ is H and X is oxygen;
g. Compounds in which $R_3$ is lower monovalent unsaturated aliphatic hydrocarbon and X is oxygen or the group H,OR$_4$
h. Compounds in which $R_3$ is lower alkinyl and X is oxygen.

Compounds of this invention, in addition to those shown in the following examples, include:

17β-hydroxy-18-propyl-15α,16α-methylene-4-estren-3-one,

17β-acetoxy-18-propyl-15α,16α-methylene-4-estren-3-one,

17β-hydroxy-18-propyl-17α-ethinyl-15α,16α-methylene-4-estren-3-one,

17β-hydroxy-18-propyl-17α-chloroethinyl-15α,16α-methylene-4-estren-3-one,

17β-acetoxy-18-propyl-17α-ethinyl-15α,16α-methylene-4-estren-3-one,

17β-heptanoyloxy-18-propyl-17α-ethinyl-15α,16α-methylene-4-estren-3-one,

3β,17β-dihydroxy-18-propyl-17α-ethinyl-15α,16α-methylene-4-estren-3-one.

Since the compounds of the present invention exhibit valuable steroid hormone properties, they can be used as pharmaceuticals. Accordingly, the use of the compounds of this invention as drugs and/or in drugs is likewise the subject of the present invention.

The steroids of Formula I wherein $R_3$ is hydrogen possess, inter alia, strong anabolic and androgenic activity. For example, 18-methyl-15α,16α-methylene-19-nortestosterone (A) is superior to the standard compound testosterone propionate (B) in the conventional seminal vesicle, prostate, and musculus levator ani tests described in R. I. Dorfman, Methods in Hormone Research, Academic Press, New York and London, 1969, vol. IIa, p. 151 f.

In Table 1, the comparative seminal vesicle, prostate, and musculus levator and effects obtained upon subcutaneous administration of A and B, respectively, to castrated rats are compared with each other. The resultant data clearly demonstrate the superior effectiveness of the compounds of this invention.

TABLE I

| | COMPOUND | DOSE (mg./animal/day) | Weight of Seminal Vesicle (mg.) | Weight of Prostate (mg.) | Weight of Musculus Levator Ani (mg.) |
|---|---|---|---|---|---|
| A | 18-methyl-15α,16α-methylene-19-nortestosterone | 3 | 509 | 319 | 63 |
| B | Testosterone propionate | 10 | 456 | 298 | 68 |

By comparison, the steroids of Formula I wherein $R_3$ represents, inter alia, an unsaturated alkyl residue, are distinguished by strong gestagenic activity. For example, 18methyl-17α-ethinyl-15α,16α-methylene-19-nortestosterone (C) proves to be superior to the conventional 18-methyl-17α-ethinyl-19-nortestosterone (D) in the fertilization inhibition test as well as in the conventional Clauberg test described in W. Elger etal. Acta Endocrinol., Suppl. 152 (1971) 71, and R. I. Dorfman, Methods in Hormone Research, Academic Press, New York and London, 1962, vol. II, p. 127 f. respectively. In Table 2, the results are set forth with subcutaneous administration of (C) and (D) to rabbits in the fertilization inhibition test and in the Clauberg test.

TABLE 2

| | COMPOUND | Fertilization inhibition test | | Clauberg Test | |
|---|---|---|---|---|---|
| | | Dose (mg.) | Effect | Dose (mg.) | McPhail* |
| C | 18-methyl-17α-ethinyl-15α,16α-methylene-19-nortestosterone | 0.3 | Active | 0.01 | 2.2 |
| D | 18-methyl-17α-ethinyl-19-nortestosterone | 0.5 | Inactive | 0.01 | 1.0 |

*McPhail scale: 1 = no effect; 4 = complete transformation of endometrium (gestagenic activity)

The higher activity, i.e., the superior effectiveness of the compounds of this invention is clearly shown by the above comparison.

The higher esters of the compounds of this invention are furthermore distinguished by a protracted effectiveness.

The androgenic compounds of this invention can be employed, inter alia, for the treatment of diseases due to androgen deficiency or wherein the administration of androgens is indicated. The gestagenic compounds can be utilized, e.g., in contraceptive preparations wherein they are used either as the gestagenic component in combination with an estrogenically effective hormone component, e.g., ethinylestradiol, or as the sole effective component. The gestagenic compounds can also be employed in preparations for the treatment of gynecological disturbances.

Consequently, the androgenic compounds of this invention can be used, for example, for the treatment of the lessening of male functional power in middle age and old age; cardiac and circulatory disorders; potency disturbances; hypogonadism, etc., muscular dystrophy, etc.

The gestagenic compounds of this invention can be advantageously employed for the treatment of the following gynecological conditions: primary and secondary amenorrhea, endometriosis, hypoplasia uteri, functional bleeding, glandular cystic hyperplasia, sterility caused by dysfunction of the corpus luteum, cycle aberrations, premenstrual discomforts, mastopathia, etc., and contraception.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparation can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees or capsules having talc and/or a carbohydrate carrier or binder or the like, the carrier preferably being lactose and/or corn starch and/or potato starch. A syrup, elixir, or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of the invention are dispensed in unit dosage form comprising 1–500 mg. of a pharmaceutical carrier per each unit dosage, and the amount per unit dosage is about 0.01 mg. to 100 mg. preferable about 0.03 to 50 mg., of active agent of this invention.

The compounds of this invention are generally administered to animals, including but not limited to mammals, e.g., humans. An androgenically anabolically effective daily dosage of the active compounds as administered subcutaneously to humans generally comprises about 0.2 to 2.0 mg/kg of body weight, together with 10 – 500 mg. of pharmaceutically acceptable carrier. A gestagenically effective daily dosage of the active compounds as administered orally to humans generally comprises about 0.001 to 0.5 mg/kg of body weight, together with 10 – 500 mg. of pharmaceutically acceptable carrier. The dose can be administered singly or as divided dosages throughout the day.

The usefulness of the compounds of this invention as androgenic and gestagenic, respectively, agents has been established in laboratory test animals. Subcuteneous administration is preferred for androgenically/anabolically active compounds, the compounds of this invention being particularly valuable in the treatment of humans afflicted with androgen deficiency. Oral administration is preferred for gestagenically active compounds, the compounds of this invention being particularly valuable in the treatment of humans afflicted with gynaecological disturbances or for preventing conception. In this regard, the compounds of this invention can be employed in substantially the same manner as the known compounds testosterone propionate and 18-methyl-17α-ethinyl-19-nor-testosterone, respectively.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

The compounds of this invention can also be intermediates for those pharmacologically valuable steroids which are obtained by conventional conversion methods, such as, for example rearrangement, hydrogenation, dehydrogenation, etc.

The 15α,16α-methylene-4-estren-17β-ols of Formula I are prepared by reducing a 15α,16α-methylene-17-oxo-5(6)-and/or -5(10)-estrene of Formula II.

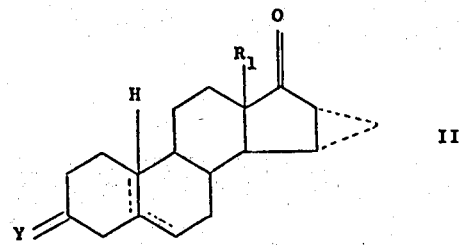

II wherein $R_1$ has the above indicated values and Y is a keto group preferably masked as the ketal, in accordance with the conventional reduction methods; optionally an unsaturated 17α-alkyl residue is hydrogenated, a primarily introduced keto masking group is split off, and, depending on the finally desired value of X, $R_2$ and $R_4$, thereafter optionally the 17-hydroxy group is esterified and/or the 3-keto group is reduced and free hydroxy groups present in the molecule are esterified in a conventional manner.

The reduction of the 17-keto group can be effected by hydrogenation in the presence of a hydrogenation catalyst suitable for accomplishing the reduction of five-membered-ring ketones in the presence of hydrogen. Furthermore, the hydrogen can be transferred to the 17-ketone of Formula II as a metal hydride. Especially suitable hydrogen donors are the complex alkali metal hydrides, sodium hydridoborate, lithium hydridoaluminate, sodium hydridotrimethoxoborate and lithium hydridotri-tert.-butoxoaluminate.

The reduction can also be effected according to known methods with an organometallic compound wherein the organic residue is $R_3$ and wherein the compound can be an alkyl magnesium halide, e.g., methylmagnesium bromide or iodide; an alkenyl magnesium halide and/or alkenyl zinc halide, e.g., vinylmagnesium bromide or allylmagnesium bromide; and alkinyl magnesium halide, e.g., ethinylmagnesium bromide, propinylmagnesium bromide, or propinylzinc bromide; or an alkali metal acetylide, e.g., potassium acetylide. The organometallic compound utilized as the reducing agent can also be formed in situ and made to react with the 17-ketone of Formula II. Thus, for example, the ketone is treated, for the reaction with organometallic alkinyl compounds, in a suitable solvent, with an alkine, chloroalkine, or alkadiyne and an alkali metal, preferably in the presence of a tertiary alcohol or in the presence of ammonia and optionally under elevated pressure.

In a preferred mode of operation, the reduction of the 17-keto group is effected in the presence of a masked 3-keto group, e.g., a ketal. The ketal residues are derived from the alcohols customarily employed for the masking of free oxo groups; examples are ethylene glycol and 2,2-dimethyl-1,3-propanediol.

The unsaturated 17α-alkyl residues can be converted into the corresponding 17α-alkenyl and/or 17α-alkyl steroids by hydrogenation. As is know, this hydrogenation is preferably conducted by reacting steroids having an unsaturated 17α-alkyl residue with hydrogen in the presence of a hydrogenation catalyst. Suitable hydrogenation catalysts include but are not limited to palladium catalysts or platinum oxide catalysts, optionally on supports.

The reduction of the 3-keto group can be conducted in accordance with methods known in the art. This process can be accomplished, for example, by hydrogenation in the presence of a conventional catalyst effecting, in the presence of hydrogen, the reduction of unsaturated six-membered ring ketones. This step can alternatively be conducted with metal hydrides or hydrido complexes; examples are sodium hydridoborate, lithium hydridoaluminate, sodium hydridotrimethoxoborate,, and lithium hydridotri-tert.-butoxoaluminate.

The subsequent esterification is effected by the methods usually employed for the esterification of steroid alcohols in steroid chemistry. An example for the acylation of a hydroxy group in the 3-position is the reaction with an acid anhydride in the presence of a tertiary amine at room temperature. For the esterification of a 17β-hydroxy group, one example is the reaction with acid anhydrides in the presence of strong acids, e.g., p-toluenesulfonic acid, or the reaction with an acid anhydride in the presence of a tertiary amine under heating. The last-mentioned methods can also be used for converting the 3,17-dihydroxy steroids into the diacylate.

The keto masking group is split off according to methods known in the art. For deketalization, it is possible to use mineral acids, e.g., perchloric acid, sulfuric acid, or hydrochloric acid, or organic acids, e.g., oxalic acid.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following Examples, the temperatures are set forth uncorrected in degrees Celsius.

The preparation of the 15α,16α-methylene-17-oxo-5(6)- and/or -5(10)-estrenes of Formula II used as the starting compounds in the form of the ketals is described by the following Examples A and B.

A.
3,3-(2',2'-dimethyl-1',3'-propylenedioxy)-18-methyl-15α,16α-methylene-5(6)- and/or -5(10)-estren-17-one 46.2 g. of natural (i.e., having the steric configuration of the naturally occurring optically active pregnane steroids) 18-methyl-19-nor-4,16-pregnadiene-3,20-dione is refluxed in 2.5 liters of benzene with 37.1 g. of 2,2-dimethyl-1,3-propanediol and 2.7 g. of p-toluenesulfonic acid for 6 hours with the use of a water trap. After cooling, the reaction solution is washed with saturated sodium bicarbonate solution and water, dried over sodium sulfate, and evaporated to dryness under vacuum. The thus-obtained residue is chromatographed on silica gel and, after recrystallisation from diisopropyl ether, 28.6 g. of natural 3,3-(2',2'-dimethyl-1',3'-propylenedioxy)-18-methyl-19-nor-5,16- und-/or -5(10),16-pregnadien-20-one is obtained, m.p. 145°–155° C.

UV: $C_{243}$ = 8,530.

38.2 g. of natural 3,3-(2',2'-dimethyl-1',3'-propylenedioxy)-18-methyl-19-nor-5,16- and/or -5(10),16-pregnadien-20-one, dissolved in 229 ml. of tetrahydrofuran, is added dropwise over 30 minutes to a solution of 29.2 g. potassium tert.-butylate in 343 ml. dimethylformamide, 57 ml. absolute tert.-butanol, and 22.9 ml. trimethyl phosphite cooled to −20° C. while oxygen is being passed through the reaction mixture. Thereafter, the mixture is agitated for another hour at −20° C. while oxygen is passed therethrough. The reaction solution is then stirred into weakly acidic ice water; the thus-obtained precipitate is filtered off, washed thoroughly with water, dissolved in methylene chloride, and dried over sodium sulfate. The residue obtained after evaporation is chromatographed on silica gel, thus producing, after recrystallisation from diisopropyl ether/methylene chloride, 15.5 g. of natural 17-hydroxy-3,3-(2',2'-dimethyl-1',3'-propylenedioxy)-18-methyl-19-nor-5,15-and/or -5(10),15-pregnadien-20-one, m.p. 202°–214° C.

14.0 g. of natural 17-hydroxy-3,3-(2',2'-dimethyl-1',3'-propylenedioxy)-18-methyl-19-nor-5,15- and/or -5(10),15-pregnadien-20-one is dissolved in 140 ml. of absolute tetrahydrofuran, mixed with 14.0 g. of lithium tri-tert.-butoxyalanate and allowed to stand for 1 hour at room temperature. The reaction solution is then stirred into ice water, acidified with dilute sulfuric acid, and extracted with methylene chloride. The crude product obtained after drying and evaporation is chromatographed on silica gel, yielding 13.0 g. of natural 17,20ξ-dihydroxy-3,3-(2',2'-dimethyl-1',3'-propylenedioxy)-18-methyl-19-nor-5,15- and/or 5(10),15-pregnadiene.

10.4 g. of natural 17,20ξ-dihydroxy-3,3-(2',2'-dimethyl-1',3'-propylenedioxy)-18-methyl-19-nor-5,15- and/or 5(10),15-pregnadiene is refluxed for 5 hours in 185 ml. of absolute ether and 185 ml. of absolute ethylene glycol dimethyl ether with 16.8 ml. of methylene iodide and 20.8 g. of zinc-copper. The mixture is then diluted with methylene chloride, washed with saturated aqueous ammonium chloride solution and water, dried over sodium sulfate, and evaporated to dryness under vacuum. The residue is chromatographed on silica gel, yielding 6.8 g. of natural 17,20$\xi$-dihydroxy-3,3-(2',2'-dimethyl-1',3'-propylenedioxy)-18-methyl-15$\alpha$,16$\alpha$-methylene-19-nor-5- and/or -5(10)-pregnene.

9.0 g. of natural 17,20$\xi$-dihydroxy-3,3-(2',2'-dimethyl-1',3'-propylenedioxy)-18-methyl-15$\alpha$,16$\alpha$-methylene-19-nor-5- and/or -5(10)-pregnene is mixed, in 360 ml. of methylene chloride, with 27 g. of pyridine - chromic acid complex produced by reacting chromium(VI) oxide in pyridine and isolating the thus-precipitated complex, and the resultant mixture is stirred for 3 hours at room temperature. The reaction solution is filtered via a porous plate, and the filtrate is evaporated to dryness under vacuum. The residue is chromatographed on silica gel, thus yielding 3.9 g. of natural 3,3-(2',2'-dimethyl-1',3'-propylenedioxy)-18-methyl-15$\alpha$,16$\alpha$-methylene-5- and/or -5(10)-estren-17-one.

B.

3,3-(2',2'-dimethyl-1',3'-propylenedioxy)-15$\alpha$,16$\alpha$-methylene-5(6)- and/or -5(10)-estren-17-one 5.0 g. 19-nor-4,16-pregnadiene-3,20-dione is refluxed in 250 ml. of benzene with 4.0 g. of 2,2-dimethyl-1,3-propanediol and 300 mg. of p-toluenesulfonic acid for 2 hours using a water trap. The mixture is worked up as described in Example A. After chromatography on silica gel, 4.9 g. of 3,3-(2',2'-dimethyl-1',-3'-propylenedioxy)-19-nor-5,16- and/or -5(10),16-pregnadien-20-one is obtained.

UV: $\epsilon_{239} = 9,200$.

5.0 g. of 3,3-(2',2'-dimethyl-1',3'-propylenedioxy)-19-nor-5,16- and/or 5(10),16-pregnadien-20-one is reacted with potassium tert.-butylate solution, oxygen, and trimethyl phosphite at $-5°$ C. and worked up as described in Example A. After chromatography on silica gel and recrystallisation from diisopropyl ether/methylene chloride, one obtains 1.5 g. of 17-hydroxy-3,3-(2',2'-dimethyl-1',3'-propylenedioxy)-19-nor-5,15- and/or -5(10),15-pregnadien-20-one, m.p. 241°–249° C.

44.5 g. of 17-hydroxy-3,3-(2',2'-dimethyl-1',3'-propylene-dioxy)-19-nor-5,15- and/or -5(10),15-pregnadien-20-one is reacted with 45 g. of lithium tri-tert.-butoxyalanate in 440 ml. of absolute tetrahydrofuran and worked up as described in Example A. After chromatography on silica gel, 37.6 g. of 17,20$\xi$-dihydroxy-3,3-(2',2'-dimethyl-1',3'-propylenedioxy)-19-nor-5,15- and/or -5(10),15-pregnadiene is obtained.

35.6 of 17,20$\xi$-dihydroxy-3,3-(2',2'-dimethyl-1',3'-propylenedioxy)-19-nor-5,15- and/or 5(10),15-pregnadiene is refluxed for 6.5 hours under agitation in 475 ml. of absolute ether and 475 ml. of absolute ethylene glycol dimethyl ether with 57.3 ml. of methylene iodide and 71.2 g. of zinc-copper. The reaction mixture is worked up as set forth in Example A, thus obtaining, after chromatography on silica gel, 17.7 g. of 17,20$\xi$-dihydroxy-3,3-(2',2'-dimethyl-1',3'-propylenedioxy)-15$\alpha$,16$\alpha$-methylene-19-nor-5-and/or -5(10)-pregnene.

17 g. of 17,20$\epsilon$-dihydroxy-3,3-(2',2'-dimethyl-1',3'-propylenedioxy)-15$\alpha$,16$\alpha$-methylene-19-nor-5- and/or -5(10)-pregnene is reacted in 1.35 ml. of methylene chloride with 51 g. of pyridine-chromic acid complex for 1 hour at room temperature and then worked up as described in Example A. After chromatography on silica gel, 7.4 g. of 3,3-(2',2'-dimethyl-1',3'-propylenedioxy)-15$\alpha$,16$\alpha$-methylene-5- and/or -5(10)-estren-17-one is obtained. A sample recrystallized from hexane melts at 173°–177° C.

From the ketals, the free oxo compounds can be prepared in accordance with conventional methods.

The following examples explain the invention without limiting same:

EXAMPLE 1

12.0 g. of natural 3,3-(2',2'-dimethyl-1',3'-propylenedioxy)-18-methyl-15$\alpha$,16$\alpha$-methylene-5- or -5(10)-estren-17-one is mixed in 200 ml. of absolute tetrahydrofuran with 12.0 g. of lithium tri-tert.-butoxyalanate and agitated for 1 hour at room temperature. The mixture is then stirred into ice water, acidified with dilute sulfuric acid, extracted with methylene chloride, and the methylene chloride phase washed neutral. After drying, evaporation, and chromatography on silica gel, 11.5 g. of natural 3,3-(2',2'-dimethyl-1',3'-propylenedioxy)-18-methyl-15$\alpha$,-16$\alpha$-methylene-5- or -5(10)-estren-17$\beta$-ol is obtained.

EXAMPLE 2

11.5 g. of natural 3,3-(2',2'-dimethyl-1',3'-propylenedioxy)-18-methyl-15$\alpha$,16$\alpha$-methylene-5- or -5(10)-estren-17$\beta$-ol is refluxed in 414 ml. of methanol with 8.3 g. of oxalic acid in 83 ml. of water for 2.5 hours. The mixture is then stirred into ice water, the thus-obtained precipitate is filtered off and dissolved in methylene chloride. The residue obtained after drying and evaporation is chromatographed on silica gel, thus obtaining 7.0 g. of natural 17$\beta$-hydroxy-18-methyl-15$\alpha$,16$\alpha$-methylene-4-estren-3-one.

UV: $\epsilon_{240} = 16,200$.

EXAMPLE 3

2.0 g. of 3,3-(2',2'-dimethyl-1',3'-propylenedioxy)-15$\alpha$,16$\alpha$-methylene-5- or -5(10)-estren-17-one is reacted in 30 ml. of absolute tetrahydrofuran with 2.0 g. of lithium tri-tert.-butoxyalanate, as described in Example 1, and worked up, thus producing 1.95 g. of 3,3-(2',2'-dimethyl-1',3'-propylenedioxy)-15$\alpha$,16$\alpha$-methylene-5- or -5(10)-estren-17$\beta$-ol.

EXAMPLE 4

1.95 g. of 3,3-(2',2'-dimethyl-1',3'-propylenedioxy)-15$\alpha$,16$\alpha$-methylene-5- or -5(10)-estren-17$\beta$-ol is refluxed in 70 ml. of methanol with 1.4 g. of oxalic acid in 14 ml. of water for 3 hours. After working the reaction mixture up as set forth in Example 1, and chromatography on silica gel, 1.5 g. of 17$\beta$-hydroxy-15$\alpha$,16$\alpha$-methylene-4-estren-3-one is produced.

UV: $\epsilon_{239} = 17,500$.

EXAMPLE 5

900 mg. of magnesium filings are reacted in 13 ml. of absolute tetrahydrofuran with 2.93 ml. of ethyl bromide to obtain ethylmagnesium bromide. This solution is added dropwise under ice cooling into 26 ml. of absolute tetrahydrofuran, through wich is passed acetylene. A solution of 900 mg. of natural 3,3-(2',2'-dimethyl-1',3'-propylenedioxy)-18-methyl-15$\alpha$,16$\alpha$-methylene-5- or -5(10)-estren-17-one in 25 ml. of absolute tetrahydrofuran is added to this solution of ethinylmagnesium bromide, and the mixture is agitated for 3 hours at room temperature. The excess Grignard reagent is then mixed with saturated ammonium chloride solution, and the aqueous phase is extracted with ether. After drying and evaporation, 910 mg. of natural 3,3-(2',2'-dimethyl-1',3'-propylenedioxy)-18-methyl-17α-ethinyl-15α,16α-methylene-5- or -5(10)-estren-17β-ol is produced.

EXAMPLE 6

900 mg. of crude natural 3,3-(2',2'-dimethyl-1',3'-propylenedioxy)-18-methyl-17α-ethinyl-15α,16α-methylene-5- or -5(10)-estren-17β-ol is refluxed for 45 minutes in 10 ml. of methanol with 1.08 g. of oxalic acid in 2.5 ml. of water. The mixture is then diluted with ether, washed neutral with water, dried, and evaporated to dryness under vacuum. The residue is chromatographed on silica gel and, after recrystallization from diisopropyl ether, 500 mg. of natural 17β-hydroxy-18-methyl-17α-ethinyl-15α,16α-methylene-4-estren-3-one is obtained. m.p. 189.5° – 191° C.

UV: $\epsilon_{240} = 17,200$.

EXAMPLE 7

2.0 g. of magnesium filings are reacted, as described in Example 5, to ethinylmagnesium bromide, mixed with 2.0 g. of 3,3-(2',2'-dimethyl-1',3'-propylenedioxy)-15α,16α-methylene-5- or -5(10)-estren-17-one in 20 ml. of absolute tetrahydrofuran, and agitated for 2.5 hours at room temperature. After the reaction mixture has been worked up, 2.0 g. of 3,3-(2',2'-dimethyl-1',3'-propylenedioxy)-17α-ethinyl-15α,16α-methylene-5- or -5(10)-estren-17β-ol is obtained.

EXAMPLE 8

2.0 g. of crude 3,3-(2',2'-dimethyl-1',3'-propylenedioxy)-17α-ethinyl-15α,16α-methylene-5- or -5(10)-estren-17β-ol is mixed in 20 ml. of methanol with 2.0 g. of oxalic acid in 2.2 ml. of water, and refluxed for 2 hours. The mixture is worked up as set forth in Example 6. After chromatography on silica gel, the product is recrystallized from diisopropyl ether/methylene chloride, yielding 1.2 g. of 17β-hydroxy-17α-ethinyl-15α,16α-methylene-4-estren-3-one, m.p. 145°–146° C.

UV: $\epsilon_{239} = 17,700$.

EXAMPLE 9

5.0 g. of natural 17β-hydroxy-18-methyl-15α,16α-methylene-4-estren-3-one is allowed to stand at room temperature in 20 ml. of pyridine and 10 ml. of acetic anhydride for 18 hours. The mixture is then stirred into ice water, the thus-obtained precipitate is filtered off and dissolved in methylene chloride. The methylene chloride phase is washed successively with dilute hydrochloric acid, water, sodium bicarbonate solution, and water. After drying and evaporation, 5.5 g. of natural 17β-acetoxy-18-methyl-15α,16α-methylene-4-estren-3-one is obtained.

UV: $\epsilon_{240} = 17,100$.

EXAMPLE 10

1.0 g. of 17β-hdyroxy-15α,16α-methylene-4-estren-3-one is reacted in 4 ml. of pyridine with 2 ml. of acetic anhydride, as described in Example 9, and then worked up. After recrystallization from hexane, the yield is 820 mg. of 17β-acetoxy-15α,16α-methylene-4-estren-3-one, m.p. 139.5° – 140.5° C.

UV: $\epsilon_{239} = 18,000$.

EXAMPLE 11

600 mg. of natural 17β-hydroxy-18-methyl-17α-ethinyl-15α,16α-methylene-4-estren-3-one is refluxed in 2 ml. of acetic anhydride and 2 ml. of pyridine under a nitrogen stream for 10 hours. The mixture is then stirred into ice water, the thus-produced precipitate is filtered off, washed with water, and dried. In order to split the thus-formed 3-enolacetate, the mixture is taken up in 30 ml. of methanol and refluxed with 0.3 ml. of concentrated hydrochloric acid for 15 minutes. After precipitation in ice water, the precipitate is filtered off, washed with water, and dried. Chromatography on silica gel yields 510 mg. of natural 17β-acetoxy-18-methyl-17α-ethinyl-15α,16α-methylene-4-estren-3-one. A sample recrystallized from diisopropyl ether melts at 167.5° – 169.5° C.

UV: $\epsilon_{240} = 17,600$.

EXAMPLE 12

500 mg. of natural 17β-hydroxy-18-methyl-17α-ethinyl-15α,16α-methylene-4-estren-3-one is heated in 2 ml. of butyric acid anhydride and 2 ml. of pyridine to 160° C. for 10 hours under a nitrogen stream. The mixture is then worked up as set forth in Example 11, and the 3-enol ester is split. After chromatography on silica gel, 450 mg. of natural 17β-butyryloxy-18-methyl-17α-ethinyl-15α,16α-methylene-4-estren-3-one is obtained. A sample recrystallized from pentane melts at 118°–122° C.

UV: $\epsilon_{240} = 16,900$.

EXAMPLE 13

500 mg. of natural 17β-hydroxy-18-methyl-17α-ethinyl-15α,16α-methylene-4-estren-3-one is heated in 2 ml. of enanthic acid anhydride and 2 ml. of pyridine for 17 hours in a nitrogen stream to 170° C. The mixture is then worked up as indicated in Example 11, and the 3-enol ester is split. The excess enanthic acid is removed by steam distillation. The product obtained after ether extraction is chromatographed on silica gel, thus producing 380 mg. of natural 17β-heptanoyloxy-18-methyl-17α-ethinyl-15α,16α-methylene-4-estren-3-one in the form of an oil.

UV: $\epsilon_{240} = 17,000$.

EXAMPLE 14

400 mg. of 17β-hydroxy-17α-ethinyl-15α,16α-methylene-4-estren-3-one is reacted in 2 ml. of acetic anhydride and 2 ml. of pyridine, as described in Example 11, and worked up. After chromatography on silica gel, the yield is 390 mg. of 17β-acetoxy-17α-ethinyl-15α,16α-methylene-4-estren-3-one.

UV: $\epsilon_{240} = 17,100$.

EXAMPLE 15

150 mg. of 17β-hydroxy-17α-ethinyl-15α,16α-methylene-4-estren-3-one is reacted in 1 ml. of butyric acid anhydride and 1 ml. of pyridine, as described in Example 11, and worked up. Chromatography on silica gel yields 130 mg. of 17β-butyryloxy-17α-ethinyl-15α,16α-methylene-4-estren-3-one.

UV: $\epsilon_{239} = 17,400$.

EXAMPLE 16

150 mg. of 17β-hydroxy-17α-ethinyl-15α,16α-methylene-4-estren-3-one is reacted in 1 ml. of enanthic acid anhydride and 1 ml. of pyridine as set forth in Example 11 and worked up. After chromatography on silica gel, 140 mg. of 17β-heptanoyloxy-17α-ethinyl-15α,16α-methylene-4-estren-3-one is obtained as an oil.

UV: $\epsilon_{239} = 17,200$.

EXAMPLE 17

250 mg. of natural 17β-hydroxy-18-methyl-17α-ethinyl-15α,16α-methylene-4-estren-3-one is mixed in 20 ml. of absolute tetrahydrofuran with 800 mg. of lithium tri-tert.-butoxyalanate and stirred for 1 hour at room temperature. The mixture is then stirred into ice water, acidified with dilute sulfuric acid, extracted with methylene chloride, and the methylene chloride phase is washed neutral. After drying and evaporation, 240 mg. of a crude product is obtained. Recrystallization from diisopropyl ether yields 140 mg. of natural 3β,17β-dihydroxy-18-methyl-17α-ethinyl-15α,16α-methylene-4-estrene, m.p. 183°–187° C.

EXAMPLE 18

300 mg. of 17β-hydroxy-17α-ethinyl-15α,16α-methylene-4-estren-3-one is mixed, in 25 ml. of absolute tetrahydrofuran, with 950 mg. of lithium tri-tert.-butoxyalanate and stirred for 1 hour at room temperature. The mixture is worked up as set forth in Example 17. After chromatography on silica gel, the yield is 250 mg. of 3β,17β-dihydroxy-17α-ethinyl-15α,16α-methylene-4-estrene.

EXAMPLE 19

300 mg. of natural 3β,17β-dihydroxy-18-methyl-17α-ethinyl-15α,16α-methylene-4-estrene is allowed to stand at room temperature in 1 ml. of pyridine and with 0.5 ml. of acetic anhydride for 18 hours. The mixture is stirred into ice water, the thus-produced precipitate is filtered off, washed with water, and dried, thus obtaining 320 mg. of natural 17β-hydroxy-3β-acetoxy-18-methyl-17α-ethinyl-15α,16α-methylene-4-estrene, m.p. 117°–118.5° C.

EXAMPLE 20

250 mg. of 3β,17β-dihydroxy-17α-ethinyl-15α,16α-methylene-4-estrene is reacted in 1 ml. of pyridine with 0.5 ml. of acetic anhydride, as set forth in Example 19, and worked up, thus producing 260 mg. of 17β-hydroxy-3β-acetoxy-17α-ethinyl-15α,16α-methylene-4-estrene.

EXAMPLE 21

100 mg. of natural 3β,17β-dihydroxy-18-methyl-17α-ethinyl-15α,16α-methylene-4-estrene is refluxed in 1 ml. of pyridine and 1 ml. of acetic anhydride for 10 hours under a nitrogen stream. The mixture is then stirred into ice water; the thus-obtained precipitate is filtered off, washed with water, and dried. After chromatography on silica gel, 60 mg. of natural 3β,17β-diacetoxy-18-methyl-17α-ethinyl-15α,16α-methylene-4-estrene is produced.

EXAMPLE 22

125 mg. of 3β,17β-dihydroxy-17α-ethinyl-15,16α-methylene-4-estrene is refluxed in 1 ml. of pyridine and 1 ml. of acetic anhydride for 10 hours in a nitrogen stream. The mixture is worked up as described in Example 21. After chromatography on silica gel, the yield is 70 mg. of 3β,17β-diacetoxy-17α-ethinyl-15α,16α-methylene-4-estrene.

EXAMPLE 23

200 mg. of natural 17β-acetoxy-18-methyl-17α-ethinyl-15α,16α-methylene-4-estren-3-one is mixed in 20 ml. of absolute tetrahydrofuran with 670 mg. of lithium tri-tert.-butoxyalanate and agitated for 1 hour at room temperature. The mixture is then worked up analogously to Example 17. After chromatography on silica gel, 160 mg. of natural 3β-hydroxy-17β-acetoxy-18-methyl-17α-ethinyl-15α,16α-methylene-4-estrene is obtained.

EXAMPLE 24

150 mg. of 17β-acetoxy-17α-ethinyl-15α,16α-methylene-4-estren-3-one is mixed in 15 ml. of absolute tetrahydrofuran with 500 mg. of lithium tri-tert.-butoxyalanate and agitated for 1 hour at room temperature. The mixture is then worked up as described in Example 17. Chromatography on silica gel yields 105 mg. of 3β-hydroxy-17β-acetoxy-17α-ethinyl-15α,16α-methylene-4-estrene.

EXAMPLE 25

1.0 g. of natural 3,3-(2',2'-dimethyl-1',3'-propylenedioxy)-18-methyl-15α,16α-methylene-5- or -5(10)-estren-17-one is dissolved in 30 ml. of absolute tetrahydrofuran and introduced into a Grignard solution (produced from 1 g. of magnesium filings, 3.25 ml. of ethyl bromide, and 15 ml. of absolute tetrahydrofuran). The mixture is stirred for 4 hours at room temperature. Then, the mixture is combined with saturated ammonium chloride solution, the aqueous phase is separated, and extracted with ether. The combined organic phases are washed with water, dried, and concentrated, thus obtaining 950 mg. of crude natural 3,3-(2',2'-dimethyl-1',3'-propylenedioxy)-18-methyl-17α-ethyl-15α,16α-methylene-5- or -5(10)-estren-17β-ol.

EXAMPLE 26

300 mg. of crude natural 3,3-(2',2'-dimethyl-1',3'-propylenedioxy)-18-methyl-17α-ethyl-15α,16α-methylene-5- or -5(10)-estren-17β-ol is refluxed in 10 ml. of methanol with 300 mg. of oxalic acid in 1.5 ml. of water for 45 minutes. The mixture is worked up as set forth in Example 6. After chromatography on silica gel, 130 mg. of natural 17β-hydroxy-18-methyl-17α-ethyl-15α,16α-methylene-4-estren-3-one is produced.

UV: $\epsilon_{240} = 16,900$.

EXAMPLE 27

670 mg. of trans-dichloroethylene in 3 ml. of absolute ether is added to a methyllithium solution produced from 185 mg. of lithium and 0.83 ml. of methyl iodide in 15 ml. of absolute ether; the mixture is agitated for 1.5 hours at room temperature. To this lithium chloroacetylide solution is dropped 500 mg. of natural 3,3-(2',2'-dimethyl-1',3'-propylenedioxy)-18-methyl-15α,16α-methylene-5- or -5(10)-estren-17-one, dissolved in 20 ml. of absolute toluene within 15 minutes and the mixture is then heated under reflux for 2.5 hours. The excess reagent is then decomposed under cooling with ammonium chloride solution, the mixture is diluted with ether and washed neutral with water. After evaporation, 520 mg. of crude natural 3,3-(2',2'-dimethyl-1',3'-propylenedioxy)-18-methyl-17α-chloroethinyl-15α,16α-methylene-5- or -5(10)-estren-17β-ol is obtained.

EXAMPLE 28

520 mg. of crude natural 3,3-(2',2'-dimethyl-1',3'-propylenedioxy)-18-methyl-17α-chloroethinyl-15α,16α-methylene-5- or -5(10)-estren-17β-ol is refluxed in 20 ml. of methanol with 500 mg. of oxalic acid in 2.5 ml. of water for 45 minutes. The mixture is worked up as set forth in Example 6. Chromatography on silica gel yields 280 mg. of natural 17β-hydroxy-18-methyl-17α-chloroethinyl-15α,16α-methylene-4-estren-3-one.

UV: $\epsilon_{240} = 17,200$.

EXAMPLE 29

300 mg. of natural 3,3-(2',2'-dimethyl-1',3'-propylenedioxy)-18-methyl-17α-ethinyl-15α,16α-methylene-5- or -5(10)-estren-17β-ol is hydrogenated in 50 ml. of thiophene-free benzene with 200 mg. of Lindlar* catalyst until 2 equivalents of hydrogen have been absorbed. The reaction product is filtered off from the catalyst and evaporated to dryness under vacuum, thus obtaining 300 mg. of crude natural 3,3-(2',2'-dimethyl-1',3'-propylenedioxy)-18-methyl-17α-ethyl-15α,16α-methylene-5- or -5(10)-estren-17β-ol.

*A hydrogenation catalyst comprising palladium (cp. Fieser and Fieser "Reagents for Organic Synthesis" John Wiley and Sons, Inc., 1967, p. 566–567)

EXAMPLE 30

500 mg. of natural 17β-hydroxy-18-methyl-15α,16α-methylene-4-estren-3-one is heated in 15 ml. of collidine to the boiling point with 5 ml. of lauric acid anhydride under a nitrogen atmosphere for 5 hours. The mixture is thereafter worked up as described in Example 13. Chromatography on silica gel yields 392 mg. of 17β-dodecanoyloxy-18-methyl-15α,16α-methylene-4-estren-3-one as a viscous oil of a slightly yellow color.

UV: $\epsilon_{240} = 16,600$.

EXAMPLE 31

150 mg. of natural 3β,17β-dihydroxy-18-methyl-17α-ethinyl-15α,16α-methylene-4-estrene is allowed to stand at room temperature for 15 hours with 1 ml. of enanthic acid anhydride and 0.5 ml. of pyridine. After working the reaction mixture up as set forth in Example 19, 100 mg. of natural 17β-hydroxy-3β-heptanoyloxy-18-methyl-17α-ethinyl-15α,16α-methylene-4-estrene is obtained in the form of an oil.

EXAMPLE 32

250 mg. of natural 3β-hydroxy-17β-acetoxy-18-methyl-17α-ethinyl-15α,16α-methylene-4-estrene is allowed to stand at room temperature for 18 hours with 2.5 ml. of collidine and 1.5 ml. of caprylic acid anhydride. The reaction mixture is worked up analogously to Example 19, thus obtaining 180 mg. of 17β-acetoxy-3β-octanoyloxy-18-methyl-17α-ethinyl-15α,16α-methylene-4-estrene as an oil.

EXAMPLE 33

Small lumps of sodium (1.4 g.) are introduced into approximately 30 ml. of liquid ammonia at −80° C. to −60° C. after adding a trace of iron(III) nitrate; prior to each adding step, the blue coloring is allowed to disappear. After the addition of the alkali metal, 2.5 g. of 1,4-dichlorobutyne-2 is gradually added dropwise, and the mixture is stirred for 30 minutes. Then, 500 mg. of natural 3,3-(2',2'-dimethyl-1',3'-propylenedioxy)-18-methyl-15α,16α-methylene-5- or -5(10)-estren-17-one in 10 ml. of absolute tetrahydrofuran is added thereto, and the mixture is agitated for 2 hours at −40° C. Then, the mixture is decomposed with ammonium chloride and the ammonia is removed by evaporation at room temperature. The residue is taken up in methylene chloride, the solution washed with water, dried, and evaporated, thus obtaining 350 mg. of 3,3-(2',2'-dimethyl-1',3'-propylenedioxy)-18-methyl-17α-butadiynyl-15α,16α-methylene-5- or -5(10)-estren-17β-ol.

EXAMPLE 34

350 mg. of crude natural 3,3-(2',2'-dimethyl-1',3'-propylenedioxy)-18-methyl-17α-butadiynyl-15α,16α-methylene-5-or -5(10)-estren-17β-ol is heated in 15 ml. of methanol with 350 mg. of oxalic acid in 2 ml. of water for 45 minutes. The mixture is worked up as disclosed in Example 6. Chromatography on silica gel yields 150 mg. of natural 17β-hydroxy-18-methyl-17α-butadiynyl-15α,16α-methylene-4-estren-3-one.

UV: $\epsilon_{239} = 16,600$.

EXAMPLE 35

400 mg. of natural 3,3-(2',2'-dimethyl-1',3'-propylenedioxy)-18-methyl-17α-ethinyl-15α,16α-methylene-5- or -5(10)-estren-17β-ol is hydrogenated in 50 ml. of thiophene-free benzene with 250 mg. of Lindlar catalyst until 1 equivalent of hydrogen has been absorbed. The reaction product is filtered off from the catalyst and evaporated to dryness under vacuum, thus obtaining 350 mg. of crude natural 3,3-(2',2'-dimethyl-1',3'-propylenedioxy)-18-methyl-17α-vinyl-15α,16α-methylene-5- or -5(10)-estren-17β-ol.

EXAMPLE 36

350 mg. of crude natural 3,3-(2',2'-dimethyl-1',3'-propylenedioxy)-18-methyl-17α-vinyl-15α,16α-methylene-5- or -5(10)-estren-17β-ol is refluxed in 15 ml. of methanol with 350 mg. of oxalic acid in 2.0 ml. of water for 35 minutes. The mixture is worked up as set forth in Example 6. Chromatography on silica gel yields 230 mg. of natural 17β-hydroxy-18-methyl-17α-vinyl-15α,16α-methylene-4-estren-3-one.

UV: $\epsilon_{240} = 16,500$.

EXAMPLE 37

(Ampoules with 20 mg. of Effective Agent)

2 g. of 18-methyl-15α,16α-methylene-19-nortestosterone is dissolved in sesame oil so as to make 100 ml. Then, the solution is filled into ampoules in 1 ml. portions, and the ampoules are sterilized for 1 hour at 120° C.

EXAMPLE 38

(Ampoules with 50 mg. of Effective Agent)

5 g. of 18-methyl-15α,16α-methylene-19-nortestosterone is dissolved in castor oil/benzyl benzoate (6:4) so as to make 100 ml. Then, the solution is filled into ampoules in 1 ml. portions, and the ampoules are sterilized for 1 hour at 120° C.

EXAMPLE 39

(Composition of a Tablet)

| | |
|---|---|
| 25.000 mg. | 18-Methyl-15α,16α-methylene-19-nortestosterone |
| 85.000 mg. | Lactose (DAB 6) |
| 8.000 mg. | Corn starch (USP XVI) |
| 1.000 mg. | Magnesium stearate (USP XVI) |
| 1.000 mg. | Talc (DAB 6) |
| 120.000 mg. | Total weight of tablet |

EXAMPLE 40

(Composition of a Tablet)

| | |
|---|---|
| 5.000 mg. | 18-Methyl-15α,16α-methylene-19-nortestosterone |
| 105.000 mg. | Lactose (DAB 6) |
| 8.000 mg. | Corn starch (USP XVI) |
| 1.000 mg. | Magnesium stearate (USP XVI) |
| 1.000 mg. | Talc (DAB 6) |
| 120.000 mg. | Total weight of tablet |

EXAMPLE 41

(Ampoules with 0.250 mg. of Effective Agent)

250 mg. of 18-methyl-17α-ethinyl-15α,16α-methylene-19-nortestosterone is dissolved in a mixture of castor oil/benzyl benzoate (6:4), and the solution is then replenished to make 1000 ml. The aseptically filtered solution is filled into 1 ml. ampoules in the usual manner under sterile conditions. The ampoules are finally subjected to a post-sterilization step for 2 hours at 120° C.

EXAMPLE 42

(Composition of a Tablet)

| | |
|---|---|
| 0.450 mg. | 18-Methyl-17α-ethinyl-15α,16α-methylene-19-nortestosterone |
| 63.250 mg. | Lactose |
| 15.000 mg. | "Avicel" |
| 1.000 mg. | Talc |
| 0.300 mg. | Magnesium stearate |
| 80.000 mg. | Total weight of tablet |

EXAMPLE 43

(Composition of a Mating Capsule)

0.250 mg. of 18-methyl-17α-ethinyl-15α,16α-methylene-19-nortestosterone is mixed with 200–210 mg. of lactose, and the mixture is filled into mating capsules, size 3.

EXAMPLE 44

(Composition of a Dragee)

| | |
|---|---|
| 0.250 mg. | 18-Methyl-17α-ethinyl-15α,16α-methylene-19-nortestosterone |
| 31.748 mg. | Lactose |
| 18.425 mg. | Corn starch |
| 2.060 mg. | Polyvinylpyrrolidone 25 |
| 0.011 mg. | Methyl p-hydroxybenzoate |
| 0.006 mg. | Propyl p-hydroxybenzoate |
| 2.500 mg. | Talc |
| 55.000 mg. | Total weight of the tablet which is coated with the usual sugar mixture to obtain a weight of about 90 mg. |

EXAMPLE 45

(Composition of a Tablet)

| | |
|---|---|
| 0.030 mg. | 18-Methyl-17α-ethinyl-15α,16α-methylene-19-nortestosterone |
| 63.670 mg. | Lactose |
| 15.000 mg. | "Avicel" |
| 1.000 mg. | Talc |
| 0.300 mg. | Magnesium stearate |
| 80.000 mg. | Total weight of tablet |

EXAMPLE 46

(Composition of a Dragee)

| | |
|---|---|
| 0.250 mg. | 18-Methyl-17α-ethinyl-15α,16α-methylene-19-nortestosterone |
| 0.050 mg. | 17α-Ethinylestradiol |
| 31.700 mg. | Lactose |
| 18.425 mg. | Corn starch |
| 2.060 mg. | Polyvinylpyrrolidone 25 |
| 0.010 mg. | Methyl p-hydroxybenzoate |
| 0.005 mg. | Propyl p-hydroxybenzoate |
| 2.500 mg. | Talc |
| 55.000 mg. | Total weight of the tablet which is coated with the usual sugar mixture to obtain weight of about 90 mg. |

EXAMPLE 47

(Composition of a Tablet)

| | |
|---|---|
| 0.300 mg. | 18-Methyl-17α-ethinyl-15α,16α-methylene-19-nortestosterone |
| 0.050 mg. | 17α-Ethinylestradiol |
| 63.350 mg. | Lactose |
| 15.000 mg. | "Avicel" |
| 1.000 mg. | Talc |
| 0.300 mg. | Magnesium stearate |
| 80.000 mg. | Total weight of tablet |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 15α,16α-Methylene -4-estren-17β-ols of the formula

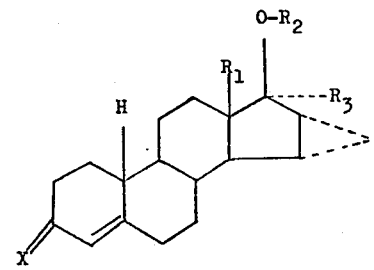

wherein $R_1$ is lower alkyl, $R_2$ is hydrogen or alkanoyl of 1-15 carbon atoms, $R_3$ is hydrogen or a monovalent lower aliphatic hydrocarbon of 1–5 carbon atoms unsubstituted or substituted by one of hydroxy or halogen, and X is oxygen or the group $H,OR_4$ wherein $R_4$ is hydrogen or alkanoyl of 1–15 carbon atoms.

2. A gestogenically active compound according to claim 1 wherein $R_3$ is a monovalent lower aliphatic hydrocarbon radical of 1–5 carbon atoms.

3. An anabolically and androgenically active compound according to claim 1 wherein $R_3$ is hydrogen.

4. A compound according to claim 2 wherein $R_3$ is alkyl.

5. A compound according to claim 2 wherein $R_3$ is alkenyl.

6. A compound according to claim 2 wherein $R_3$ is alkinyl.

7. A compound according to claim 6 wherein $R_3$ is ethinyl.

8. A compound according to claim 1 wherein $R_3$ is monovalent lower aliphatic hydrocarbon of 1–5 carbon atoms substituted by halogen.

9. A compound according to claim 8 wherein $R_3$ is substituted by chlorine.

10. A compound according to claim 9 wherein $R_3$ is chloroethinyl.

11. A compound according to claim 1 wherein $R_1$ is ethyl.

12. A compound according to claim 1 wherein $R_2$ is hydrogen.

13. A compound according to claim 1 wherein $R_2$ is lower alkanoyl.

14. A compound according to claim 1 wherein X is oxygen.

15. A compound according to claim 1 wherein X is H,$OR_4$ and $R_4$ is hydrogen.

16. A compound according to claim 1 wherein X is H,$OR_4$ and $R_4$ is lower alkanoyl.

17. A compound according to claim 1 wherein $R_1$ is ethyl, $R_3$ is hydrogen and X is oxygen.

18. A compound according to claim 1 wherein $R_1$ is ethyl, $R_3$ is ethinyl and X is oxygen.

19. A compound according to claim 1 selected from the group consisting of 17β-Hydroxy-18-methyl-15α,16α-methylene-4-estren-3-one; 17β-Hydroxy-15α,16α-methylene-4-estren-3-one; 17β-Hydroxy-18-methyl-17α-ethinyl-15α,16α-methylene-4-estren-3-one; 17β-Hydroxy-17α-ethinyl-15α,16α-methylene-4-estren-3-one; 3β,17β-Dihydroxy-18-methyl-17α-ethinyl-15α,16α-methylene-4-estrene; 3β,17β-Dihydroxy-17α-ethinyl-15α,16α-methylene-4-estrene; 17β-Hydroxy-3β-acetoxy-18-methyl-17α-ethinyl-15α,16α-methylene-4-estrene; 17β-Hydroxy-3β-acetoxy-17α-ethinyl-15α,16α-methylene-4-estrene; 17β-Hydroxy-18-methyl-17α-ethyl-15α,16α-methylene-4-estren-3-one; 17β-Hydroxy-18-methyl-17α-chloroethinyl-15α,16α-methylene-4-estren-3-one; 17β-Hydroxy-3β-heptanoyloxy-18-methyl-17α-ethinyl-15α,16α-methylene-4-estrene; 17β-Hydroxy-18-methyl-17α-butadynyl-15α,16α-methylene-4-estren-3-one and 17β-Hydroxy-18-methyl-17α-vinyl-15α,16α-methylene-4-estren-3-one.

20. A compound according to claim 1 selected from the group consisting of 17β-Acetoxy-18-methyl-15α,16α-methylene-4-estren-3-one; 17β-Acetoxy-15α,16α-methylene-4-estren-3-one; 17β-Acetoxy-18-methyl-17α-ethinyl-15α,16α-methylene-4-estren-3-one; 17β-Acetoxy-17α-ethinyl-15α,16α-methylene-4-estren-3-one; 3β,17β-Diacetoxy-18-methyl-17α-ethinyl-15α,16α-methylene-4-estrene; 3β,17β-Diacetoxy-17α-ethinyl-15α,16α-methylene-4-estrene; 3β-Hydroxy-17β-acetoxy-18-methyl-17α-ethinyl-15α,16α-methylene-4-estrene; 3β-Hydroxy-17β-acetoxy-17α-ethinyl-15α,16α-methylene-4-estrene; and 17α-Acetoxy-3β-octanoyloxy-18-methyl-17α-ethinyl-15α,16α-methylene-4-estrene.

21. A compound according to claim 1 selected from the group consisting of 17β-Butyryloxy-18-methyl-17α-ethinyl-15α,16α-methylene-4-estren-3-one; 17β-Heptanoyloxy-18-methyl-17α-ethinyl-15α,16α-methylene-4-estren-3-one; 17β-Butyryloxy-17α-ethinyl-15α,16α-methylene-4-estren-3-one; 17β-Heptanoyloxy-17α-ethinyl-15α,16α-methylene-4-estren-3-one; and 17β-Dodecanoyloxy-18-methyl-15α,16α-methylene-4-estren-3-one.

22. The compound of claim 1, 17β-hydroxy-18-methyl-15α,16α-methylene-4-estren-3-one.

23. The compound of claim 1, 17β-acetoxy-18-methyl-15α,16α-methylene-4-estren-3-one.

24. A pharmaceutical composition comprising an anabolically and androgenically effective amount of a compound according to claim 3 in combination with a pharmaceutically acceptable carrier.

25. A pharmaceutical composition comprising a gestagenically effective amount of a compound according to claim 2 in combination with a pharmaceutically acceptable carrier.

* * * * *